(12) United States Patent
Yang

(10) Patent No.: US 8,152,781 B2
(45) Date of Patent: Apr. 10, 2012

(54) SAFEGUARD CAP, INJECTION NEEDLE WITH SAFEGUARD CAP, AND MEDICAL DEVICE WITH SAFEGUARD CAP

(75) Inventor: Chek Lon Yang, Singapore (SG)

(73) Assignees: JMS Co., Ltd., Hiroshima (JP); JMS Singapore Pte Ltd, Singapore (SG)

( * ) Notice: Subject to any disclaimer, the term of this patent is extended or adjusted under 35 U.S.C. 154(b) by 428 days.

(21) Appl. No.: 10/559,319

(22) PCT Filed: Sep. 13, 2004

(86) PCT No.: PCT/JP2004/013702
§ 371 (c)(1),
(2), (4) Date: Dec. 2, 2005

(87) PCT Pub. No.: WO2006/030525
PCT Pub. Date: Mar. 23, 2006

(65) Prior Publication Data
US 2007/0016146 A1    Jan. 18, 2007

(51) Int. Cl.
*A61M 5/00* (2006.01)
(52) U.S. Cl. ......... 604/263; 215/250; 215/253; 604/192
(58) Field of Classification Search .................. 604/110, 604/111, 164.08, 187, 192, 198, 206, 240, 604/263, 905, 197, 199; 215/209, 250–257
See application file for complete search history.

(56) References Cited

U.S. PATENT DOCUMENTS

| | | | | |
|---|---|---|---|---|
| 2,104,236 A | * | 1/1938 | Mermer | 215/252 |
| 3,073,307 A | * | 1/1963 | Stevens | 604/192 |
| 4,300,678 A | * | 11/1981 | Gyure et al. | 206/364 |
| 4,334,536 A | * | 6/1982 | Pfleger | 604/193 |
| 4,475,903 A | * | 10/1984 | Steenhuisen et al. | 604/111 |
| 4,720,285 A | | 1/1988 | Pickhard | |
| 4,938,744 A | * | 7/1990 | Wharff et al. | 604/263 |
| 5,135,496 A | | 8/1992 | Vetter et al. | |
| 5,207,699 A | * | 5/1993 | Coe | 604/263 |
| 5,244,107 A | * | 9/1993 | Battegazzore | 215/252 |
| 5,366,447 A | | 11/1994 | Gurley | |
| 5,540,666 A | | 7/1996 | Barta et al. | |

(Continued)

FOREIGN PATENT DOCUMENTS

JP    59-118165    7/1984

(Continued)

*Primary Examiner* — Kevin C Sirmons
*Assistant Examiner* — Kami A Bosworth
(74) *Attorney, Agent, or Firm* — Hamre, Schumann, Mueller & Larson, P.C.

(57) ABSTRACT

A safeguard cap 1 is attached to an injection needle 10 that includes a hollow needle 11 and a holding member 12 for attaching the hollow needle 11 to a medical device. The safeguard cap 1 includes a housing part 2 for housing the hollow needle 11, a base 3 to be attached to the holding member 12, and a joint (bridges 4) for joining the housing part 2 and the base 3 to each other. The housing part 2 is formed in a tubular shape, with one end thereof being open and the other being closed. The joint is formed so as to be broken when external force for rotating the housing part 2 about its longitudinal axis that serves as a central axis is applied to the housing part 2, with the base 3 having been attached to the holding member 12.

9 Claims, 6 Drawing Sheets

U.S. PATENT DOCUMENTS

| | | | | |
|---|---|---|---|---|
| 5,785,691 | A | * | 7/1998 | Vetter et al. ................... 604/187 |
| 6,068,614 | A | * | 5/2000 | Kimber et al. ................ 604/263 |
| 6,203,529 | B1 | * | 3/2001 | Gabriel et al. ................ 604/192 |
| 2004/0116857 | A1 | * | 6/2004 | Kiehne ......................... 604/110 |
| 2004/0225258 | A1 | * | 11/2004 | Balestracci ................... 604/111 |

FOREIGN PATENT DOCUMENTS

| | | |
|---|---|---|
| JP | 60-156473 | 8/1985 |
| JP | 8-10328 | 1/1996 |
| JP | 8-206202 | 8/1996 |

* cited by examiner

SAFEGUARD CAP, INJECTION NEEDLE WITH SAFEGUARD CAP, AND MEDICAL DEVICE WITH SAFEGUARD CAP

TECHNICAL FIELD

The present invention relates to a safeguard cap to be attached to an injection needle, an injection needle with a safeguard cap, and a medical device with a safeguard cap.

BACKGROUND ART

Conventionally, used injection needles are not reused but are thrown away to prevent viral infection or the like. In the case where the needles cannot be thrown away immediately after use, in order to prevent the needles from accidentally sticking someone, the caps (see, for example, JP 8(1996)-10328 A and JP 8(1996)-206202 A) that had been put thereon when the injection needles were delivered are put on the used injection needles again.

However, conventional caps that are used for safeguarding injection needles are attached to the injection needles merely through, for instance, insertion or press fit. This poses a problem that it is difficult to judge from their appearance whether the conventional injection needles with caps being put thereon have been used or have not been used. Furthermore, in the case of conventional injection needles, there is a probability that used injection needles may be reused by mistake due to the difficulty in distinguishing therebetween.

DISCLOSURE OF THE INVENTION

Hence, an object of the present invention is to provide a safeguard cap that can facilitate the distinction between a used medical device, typified by an injection needle, and unused one, an injection needle with a safeguard cap, and a medical device with a safeguard cap.

In order to achieve the object mentioned above, a first safeguard cap of the present invention that is used for safeguarding a tip of a medical device to be inserted into a living body includes a housing part for housing the tip of a medical device, a base to be attached to a portion of the medical device that is not housed in the housing part, and a joint for joining the housing part and the base to each other. The first safeguard cap is characterized in that the housing part is formed in a tubular shape, with one end thereof being open and the other being closed, and the joint is formed so as to be broken when external force for rotating the housing part about its longitudinal axis that serves as a central axis is applied to the housing part, with the base having been attached to the portion of the medical device that is not housed in the housing part.

In order to achieve the object mentioned above, a medical device with a safeguard cap of the present invention includes a medical device to be inserted into a living body and a safeguard cap for safeguarding a tip of the medical device. The medical device with a safeguard cap is characterized in that the safeguard cap includes a housing part for housing the tip of the medical device, a base to be attached to a portion of the medical device that is not housed in the housing part, and a joint for joining the housing part and the base to each other, the housing part is formed in a tubular shape, with one end thereof being open and the other being closed. The joint is formed so as to be broken when external force for rotating the housing part about its longitudinal axis that serves as a central axis is applied to the housing part, with the base having been attached to the portion of the medical device that is not housed in the housing part.

In this context, the "medical device to be inserted into a living body" preferably is the one that would be contaminated through contact with a body fluid when it is used and thus should be thrown away after use. Specific examples thereof include disposable injection needles, catheters, and cannulas.

In order to achieve the object mentioned above, a second safeguard cap of the present invention that is used for safeguarding an injection needle including a hollow needle and a holding member for attaching the hollow needle to a medical device includes a housing part for housing the hollow needle, a base to be attached to the holding member, and a joint for joining the housing part and the base to each other. The safeguard cap is characterized in that the housing part is formed in a tubular shape, with one end thereof being open and the other being closed, and the joint is formed so as to be broken when external force for rotating the housing part about its longitudinal axis that serves as a central axis is applied to the housing part, with the base having been attached to the holding member.

Furthermore, in order to achieve the above-mentioned object, an injection needle with a safeguard cap of the present invention includes an injection needle including a hollow needle and a holding member for attaching the hollow needle to a medical device, and a safeguard cap for safeguarding the injection needle. The injection needle with a safeguard cap is characterized in that the safeguard cap includes a tubular housing part for housing the hollow needle, a base to be attached to the holding member, and a joint for joining the housing part and the base to each other, the housing part is formed in a tubular shape, with one end thereof being open and the other being closed. The joint is formed so as to be broken when external force for rotating the housing part about its longitudinal axis that serves as a central axis is applied to the housing part, with the base having been attached to the holding member.

BEST MODE FOR CARRYING OUT THE INVENTION

In the safeguard cap and the injection needle with a safeguard cap of the present invention, it is preferable that the housing part, the base, and the joint are molded into one piece to form a molded body. In this case, not only can the production cost be held down but also they can be produced easily.

Furthermore, in the safeguard cap and the injection needle with a safeguard cap of the present invention, it is preferable that the joint is formed of a plurality of bridge-like members that are provided along a circumference of the opening of the housing part at intervals. In this case, the joint can be broken surely and easily.

In this case, the number of the bridge-like members preferably is in the range from 1 to 8, particularly preferably from 2 to 6. Moreover, when it is desired that the break of the bridge-like members occurs at portions thereof located on the base side, it is preferable that the bridge-like members are formed so as to be reduced in width gradually from the housing part toward the base.

With the above-mentioned configuration, a plurality of gaps surrounded by the housing part, the base, and the bridge-like members are formed between the housing part and the base. Preferably, a projection that can fit to any one of these gaps is formed in the holding member. This allows the base to be attached to the holding member more firmly. Moreover, it is preferable that an inclined surface that inclines toward the hollow needle is formed on the hollow needle side of the projection. This allows the base to be attached to the holding member easily.

Moreover, in the safeguard cap and the injection needle with a safeguard cap of the present invention, it is preferable that the base includes a projecting part, and the base is attached to the holding member so that the projecting part is positioned on a side of a cut surface of the tip of the hollow needle or on the opposite side thereto. In this manner, the orientation of the cut surface of the hollow needle can be checked even if the tip of the injection needle cannot be observed visually and thereby the stress that the patient suffers can be alleviated.

Moreover, in the safeguard cap and the injection needle with a safeguard cap of the present invention, it is preferable that the side face of the housing part is provided with a plurality of wing-like parts protruding in the direction perpendicular to the longitudinal axis of the housing part. This allows a user to apply external force easily to the housing part.

Hereinafter, examples of the safeguard cap and the injection needle with a safeguard cap of the present invention are described with reference to FIGS. 1 to 6.

Figure 2:
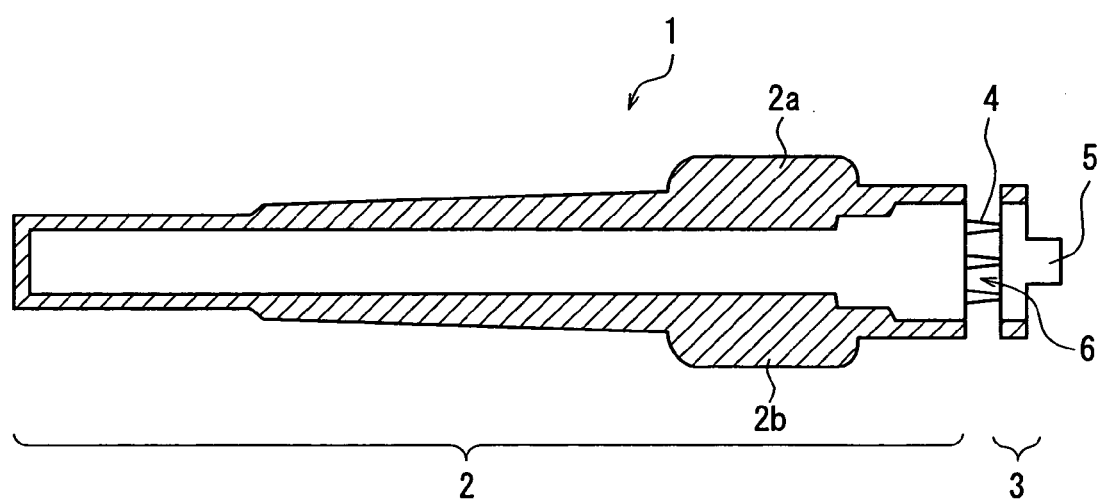
FIG. 2 is a cross-sectional view of the safeguard cap shown in FIG. 1.
Figure 3:
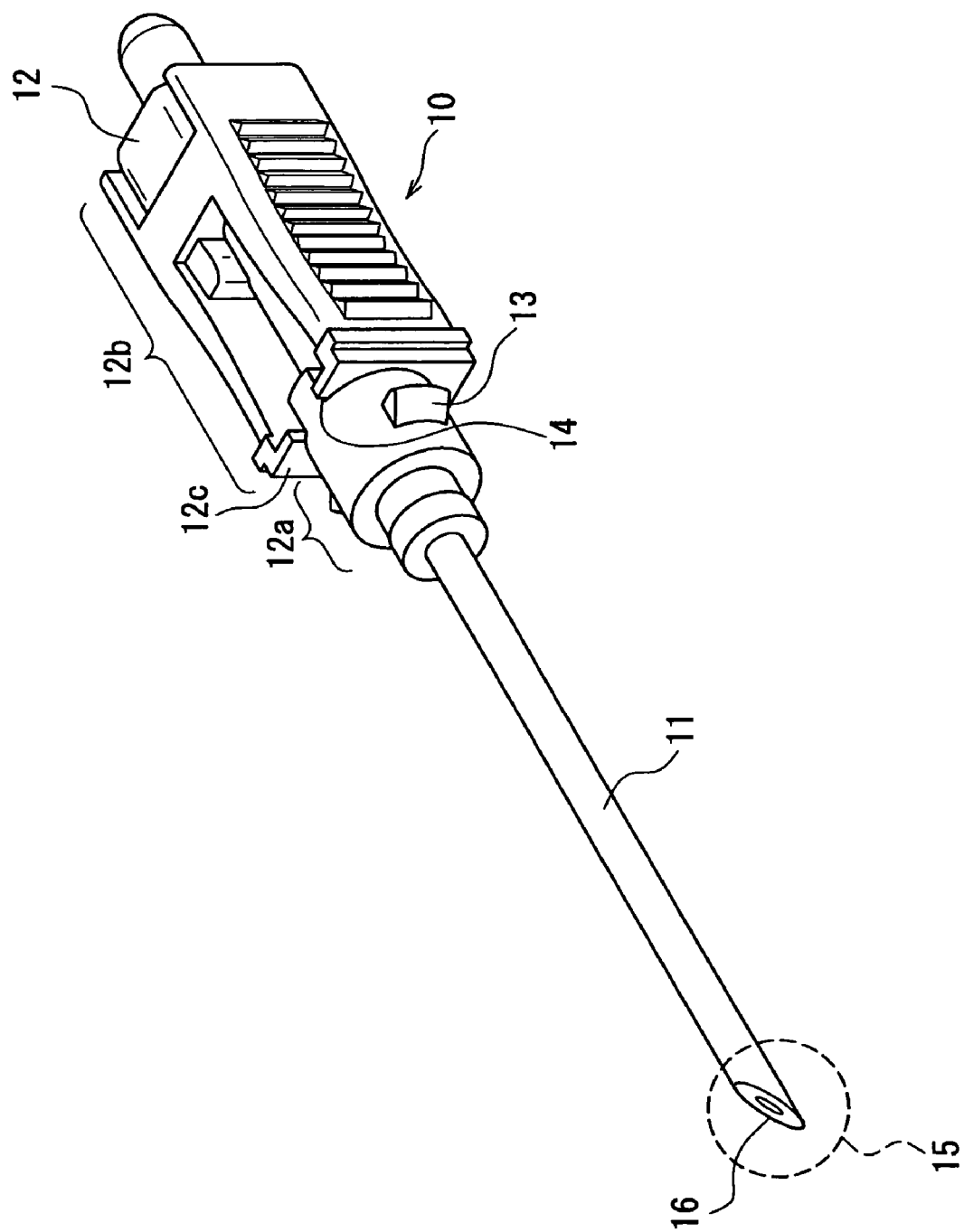
FIG. 3 is a perspective view showing an example of injection needle to which the safeguard cap shown in FIG. 1 is to be attached.

The safeguard cap of the present example is used for safeguarding an injection needle 10 shown in FIG. 3. The injection needle 10 shown in FIG. 3 includes a hollow needle 11 and a holding member 12. The holding member 12 generally is referred to as a "needle gauge" or a "needle base". The holding member 12 is used for attaching the hollow needle 11 to a medical device such as, for instance, a syringe. In the example shown in FIG. 3, the holding member 12 includes a tubular leading-end part 12a that fits into a safeguard cap 1 (see FIGS. 1 and 2) and a main body 12b.

Figure 1:
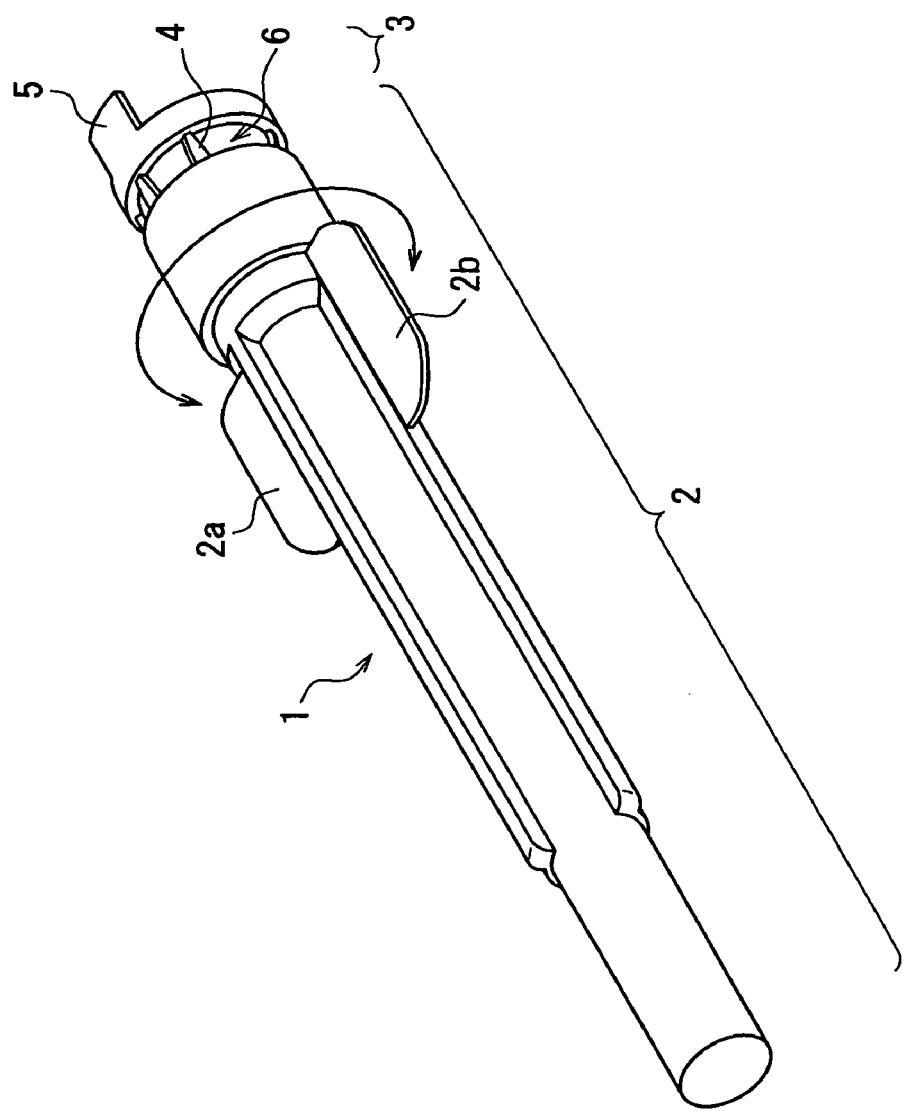
FIG. 1 is a perspective view showing an example of safeguard cap according to the present invention.

As shown in FIGS. 1 and 2, the safeguard cap 1 includes a housing part 2 that houses the hollow needle 11 (see FIG. 3), a base 3 to be attached to the holding member 12, and a joint for joining the housing part 2 and the base 3 to each other. The housing part 2 is formed in a tubular shape, with one end thereof being closed and the other being open as can be seen from FIG. 2.

In this example, the joint is formed of a plurality of bridge-like members (hereinafter referred to as "bridges") 4 that are provided along the circumference of the opening of the housing part 2 at intervals. The bridges 4 join the end face of the opening of the housing part 2 to the end face of the base 3 located on the housing part 2 side. This configuration allows gaps 6 surrounded by the housing part 2, the base 3, and the bridges 4 to be formed between the housing part 2 and the base 3.

Furthermore, the respective bridges 4 are formed so as to be broken when external force for rotating the housing part 2 about its longitudinal axis that serves as the central axis is applied to the housing part 2, with the base 3 having been attached to the holding member 12. In this context, the "external force" denotes an external force that is applied by a user of the injection needle 10 in the directions indicated with the arrows shown in FIG. 1.

In this example, the width (the length along the circumferential direction of the housing part 2) and the thickness of the bridges 4 are determined so that the bridges 4 can be broken easily by a force that is applied by a hand of man, considering the material used for forming the bridges 4, which will be described later. The number of the bridges 4 preferably is set to 1 to 8, particularly preferably to 2 to 6.

Furthermore, as shown in FIGS. 1 and 2, in the present example, each of the bridges 4 has a shape of a quadrangular pyramid in which the width and the thickness of its end located on the base 3 side are smaller than that of its end located on the housing part 2 side. Thus, the break of the bridges 4 occurs at their ends located on the base 3 side (see FIG. 5 to be described later) when the external force is applied as described above. The reason for this is that, if the break of the bridges 4 occurs at their ends located on the housing part 2 side or at their central portions, a patient might be injured with the residual parts of the bridges 4 with sharpened ends protruding from the base 3.

In the present example, the shape of the bridges 4 is not limited to the shape shown in FIGS. 1 and 2. For example, the bridges 4 may be formed so that the width and the thickness thereof are reduced stepwise from a certain point, or they may include a groove or a recess at the position where the break should occur.

Furthermore, in the present example, as shown in FIGS. 1 and 2, the side face of the housing 2 is provided with wing-like parts 2a and 2b protruding in the direction perpendicular to the longitudinal axis of the housing part 2. The wing-like parts 2a and 2b are provided in order to allow a user to apply external force easily to the housing part 2. In the example shown in FIGS. 1 and 2, the wing-like parts 2a and 2b are molded into one piece with the housing part 2 in such a manner that the wing-like parts 2a and 2b oppose each other via the opening of the housing part 2 with their wing surfaces being in co-planar with each other. It is to be noted here that the number of the wing-like parts are not particularly limited.

In the present example, the base 3 is formed in the shape of ring into which the leading-end part 12a of the holding member 12 (see FIG. 3) can be inserted. The base 3 fits to the leading-end part 12a of the holding member 12. The end face of the base 3 located on the side opposite to the housing part 2 is provided with a projecting part 5. The projecting part 5 is used for attaching the base 3 to the holding member 12. Furthermore, the projecting part 5 also serves as a mark indicating the orientation of the cut surface 16 of the needle tip 15 of the hollow needle 11 (see FIG. 3). This will be described later.

In the present example, the housing part 2, the base 3, and the joint 4 are formed in one piece using a resin material. Examples of the resin material that can be used in the present example include engineering resins that are structurally stable, flexible, and have a suitable tensile strength. More specifically, the examples include polypropylene (PP) resin, polyoxymethylene (POM) resin, and polyethylene (PE) resin.

In the present invention, it is preferable from the viewpoints of cost and ease of manufacture that the safeguard cap 1 is molded to be formed in one piece using a resin material as described above. The method of forming the safeguard cap 1, however, is not limited thereto.

The attachment of the base 3 to the holding member 12 is described below in detail. As shown in FIG. 3, a face 12c of the main body 12b of the injection needle 10 on which the leading-end part 12a is located is provided with a notch 14 to which the projecting part 5 of the base 3 (see FIG. 1) can fit.

In addition, the leading-end part 12a is provided with projections 13. The projections 13 are formed to fit to the gaps 6 of the safeguard cap 1 (see FIGS. 1 and 2) without interfering with the bridges 4. Furthermore, in order to allow the projections 13 to fit into the gaps 6 of the safeguard cap 1 easily, an inclined surface is formed on the hollow needle 11 side of each of the projections 13. The inclined surface is formed so as to incline toward the hollow needle 11.

In the present example, the projections 13 have a cross-section in a right triangle shape. The cross-section of the projections 13, however, is not limited to this example. Also, in FIG. 3, two projections 13 are shown but an arbitrary number of projections may be provided in practice.

Figure 4:
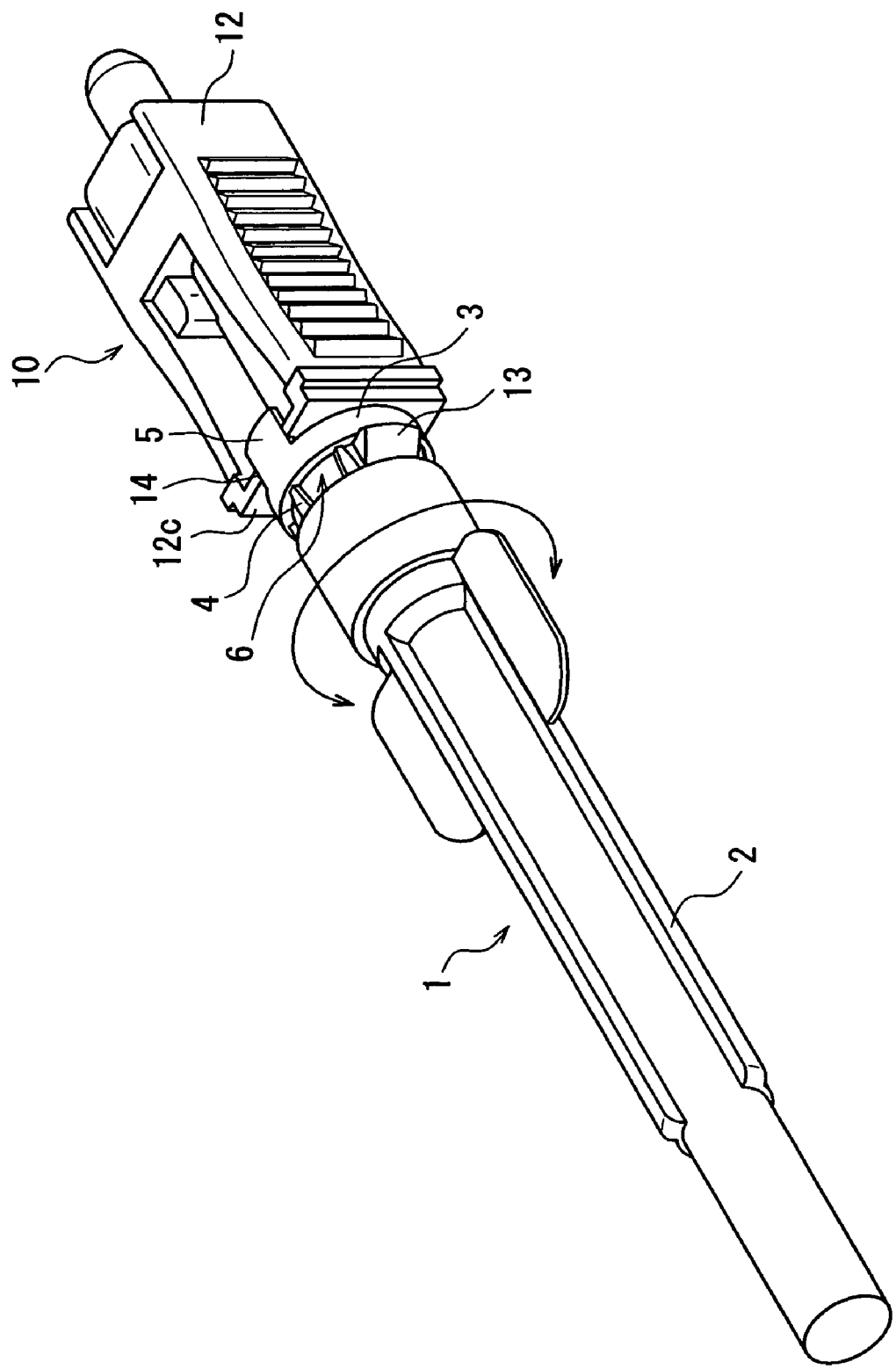
FIG. 4 is a perspective view showing an example of injection needle with a safeguard cap of the present invention.

With the hollow needle 11 being inserted into the housing part 2, the projecting part 5 is aligned with the notch 14 and then the safeguard cap 1 is put into the holding member 12. Thus, the base 3 is attached to the holding member 12 as shown in FIG. 4. As a result, the safeguard cap 1 is attached to the injection needle 10 and thereby an injection needle with a safeguard cap is obtained.

In the state shown in FIG. 4, the face 12c of the holding member 12 serves as a stopper for positioning the base 3 (see FIG. 1). The projections 13 fit into the gaps 6 formed between the housing part 2 and the base 3 and thereby the end face of the base 3 located on the housing part 2 side comes into contact with perpendicular planes of the projections 13. Thus, the base 3 is prevented from easily coming off the holding member 12.

Figure 5:
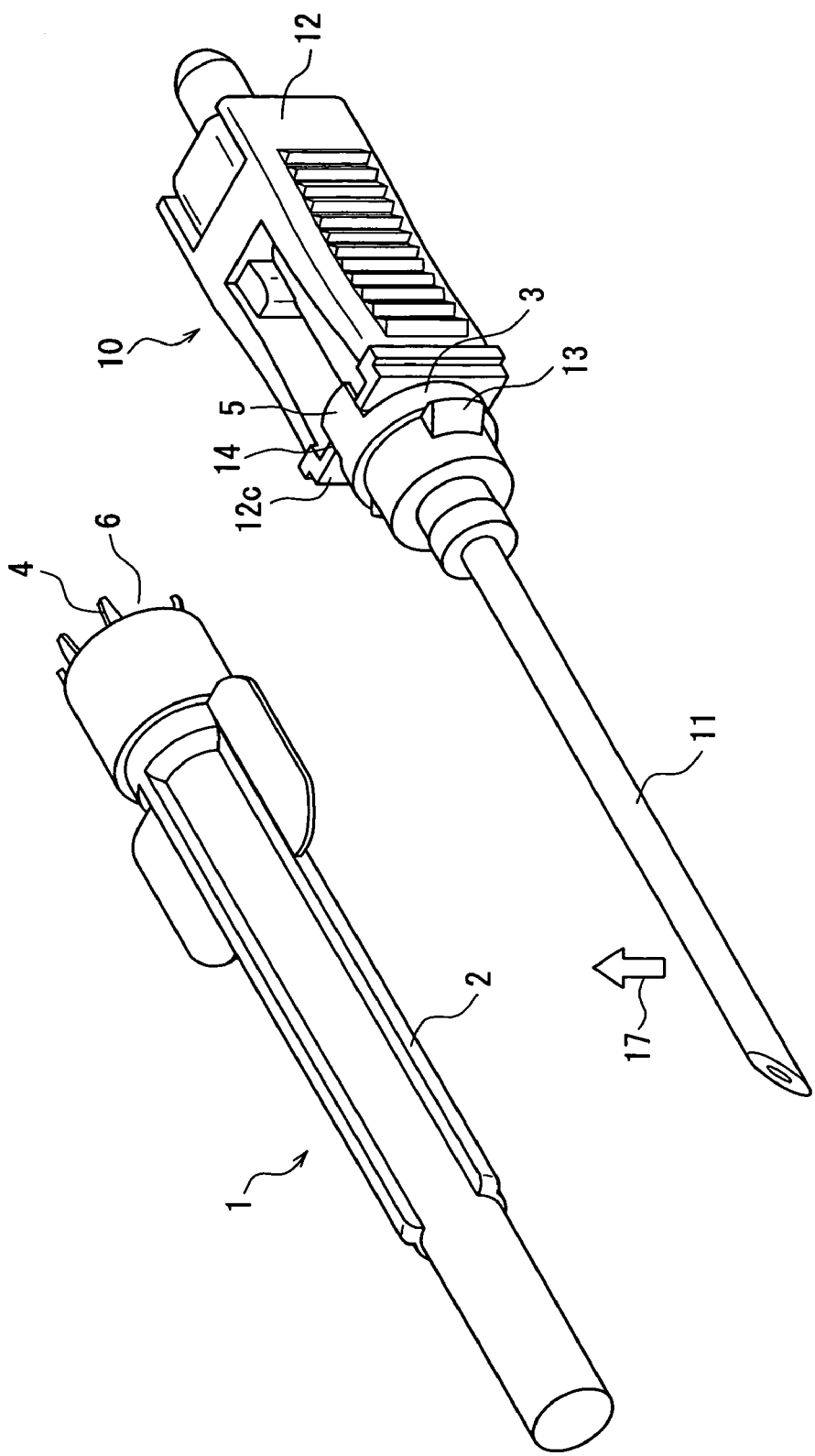
FIG. 5 is a perspective view showing the injection needle with a safeguard cap shown in FIG. 4, with the safeguard cap being removed from the injection needle.
Figure 6:
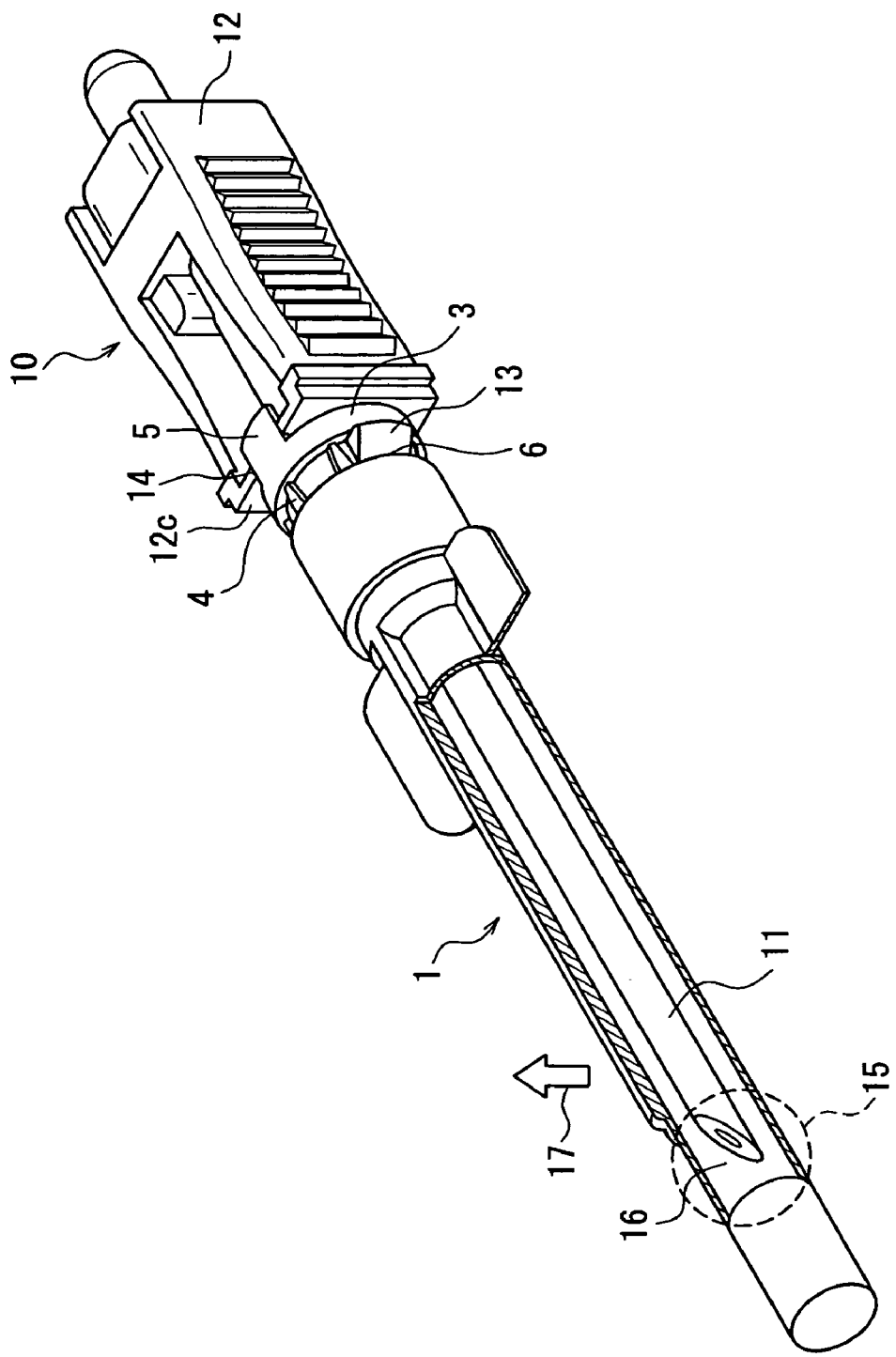
FIG. 6 is a perspective view showing the injection needle with a safeguard cap shown in FIG. 4, with part of the safeguard cap being cut away.

Furthermore, in the state shown in FIG. 4, when a user applies external force to the housing part 2 for rotating the housing part 2 about its longitudinal axis that serves as the central axis and thereby breaks the bridges 4, the housing part 2 can be detached from the injection needle 10 as shown in FIG. 5. The base 3, however, remains attached to the holding member 12.

Even if the housing part 2 is reattached to the injection needle 10 that has been used, the user can judge whether the injection needle has been used by taking a glance at the state of the bridges 4 since the bridges 4 have been broken. Accordingly, the use of the safeguard cap 1 and the injection needle 10 with the safeguard cap 1 according to the present example can prevent a used injection needle from being reused by mistake.

In the present example, the base 3 is attached to the holding member 12 through fitting. The present invention, however, is not limited to this method. It also is possible to attach the base 3 to the holding member 12 thorough gluing, screwing, etc.

When the injection needle 10 is to be inserted into the body, the orientation of the cut surface 16 of the hollow needle 11 is important (see FIG. 3). This is because, for instance, when the injection needle is used for collecting blood, the ease of drawing blood through the hollow needle depends on the orientation of the cut surface forming the tip of the injection needle. On the other hand, since the needle tip cannot be seen after the injection needle is inserted into the body, it is difficult to visually check the orientation of the cut surface. Hence, when it is intended to allow blood to be drawn easily, there is no other way than rotating the injection needle. In this case, the patient suffers heavy stress.

On the contrary, in the case of the present example, the base 3 is attached to the holding member 12, with the projecting part 5 being positioned on the side (the side indicated with the arrow 17 shown in FIG. 5) of the cut surface 16 of the tip 15 of the hollow needle 11. Hence, in the case of the present example, even when the hollow needle 11 has been inserted into the body and thereby the tip 15 cannot be seen, the user can identify the orientation of the cut surface 16 by the projecting part 5. The base 3 may be attached to the holding member 12, with the projecting part 5 being positioned on the opposite side to the cut surface 16 side.

Thus, when using the safeguard cap 1 and the injection needle 10 with the safeguard cap 1 of the present example, the injection needle 10 is not required to be rotated unnecessarily and thereby stress of the patient can be alleviated.

Industrial Applicability

As described above, when using the safeguard cap and the injection needle with a safeguard cap according to the present invention, it can be judged easily whether the injection needle has been used. Thus, the present invention can prevent infections from being caused by the reuse of used injection needles and in turn can contributes to the health of all people.

The invention claimed is:

1. An injection needle with a safeguard cap, comprising:
an injection needle including a hollow needle and a holding member for attaching the hollow needle to a medical device; and
a safeguard cap for safeguarding the injection needle,
wherein the safeguard cap comprises:
a housing part for housing the hollow needle;
a base to be attached to the holding member, and
a joint for joining the housing part and the base to each other,
the housing part is formed in a tubular shape, with one end thereof being open and the other being closed,
the base is provided with a projecting part that is engaged with the holding member so as to prevent a relative rotation between the base and the holding member;
the joint is formed of a plurality of bridge-like members that are provided along a circumference of an opening of the one end of the housing part at intervals,
the bridge-like members extend in an axial direction of the housing part so as to be joined at a tip end thereof in the axial direction to the base and are formed so as to be reduced in width gradually from the housing part toward the base, and
when the housing part of the safeguard cap is rotated about its longitudinal axis, a breaking force is applied to the bridge-like members due to the relative rotation between the housing part and the base, the bridge-like members are formed so as to be reduced in width gradually from the housing part toward the base thereby breaking the bridge-like members such that the housing part is separated from the base, with the base remaining attached to the holding member, while the bridge-like members remain with the housing part.

2. The injection needle with a safeguard cap according to claim 1, wherein the housing part, the base, and the joint are molded into one piece to form a molded body.

3. The injection needle with a safeguard cap according to claim 1, wherein the number of the bridge-like members is 1 to 8.

4. The injection needle with a safeguard cap according to claim 3, wherein a plurality of gaps surrounded by the housing part, the base, and the bridge-like members are formed between the housing part and the base,
a projection that can fit into any one of these gaps is formed in the holding member, and
an inclined surface that inclines toward the hollow needle is formed on the hollow needle side of the projection.

5. The injection needle with a safeguard cap according to claim 1, wherein the base is attached to the holding member so that the projecting part is positioned on a side of a cut surface of a tip of the hollow needle or on an opposite side thereto.

6. The injection needle with a safeguard cap according to claim 1, wherein a plurality of wing-like parts that protrude in a direction perpendicular to a longitudinal axis of the housing part are formed on a side face of the housing part.

7. The injection needle with a safeguard cap according to claim 1, wherein the bridge-like members connect the housing part and the base.

8. The injection needle with a safeguard cap according to claim 1, wherein each bridge-like member has a first end connected to the housing part, a second end connected to the base, and an elongated body defined between the first and the second ends, the first end having a greater thickness than the second end.

9. The injection needle with a safeguard cap according to claim 1, wherein a length direction of each of the bridge-like members extends between the housing part and the base.

\* \* \* \* \*